(12) United States Patent
Iwasaki et al.

(10) Patent No.: US 10,588,500 B2
(45) Date of Patent: Mar. 17, 2020

(54) ENDOSCOPE REPROCESSING TOOL

(71) Applicant: OLYMPUS CORPORATION, Tokyo (JP)

(72) Inventors: Tomokazu Iwasaki, Hachioji (JP); Mitsuyoshi Tezuka, Hachioji (JP); Hitoshi Hasegawa, Hachioji (JP); Hisato Kogure, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 36 days.

(21) Appl. No.: 16/031,313

(22) Filed: Jul. 10, 2018

(65) Prior Publication Data

US 2018/0317760 A1 Nov. 8, 2018

Related U.S. Application Data

(63) Continuation of application No. PCT/JP2017/014312, filed on Apr. 6, 2017.

(30) Foreign Application Priority Data

Apr. 25, 2016 (JP) ................................. 2016-087181

(51) Int. Cl.
*A61B 1/12* (2006.01)
*A61B 1/00* (2006.01)
(Continued)

(52) U.S. Cl.
CPC ............ *A61B 1/123* (2013.01); *A61B 1/0008* (2013.01); *A61B 1/00098* (2013.01);
(Continued)

(58) Field of Classification Search
CPC ... A61B 1/0008; A61B 1/00098; A61B 1/123; A61B 1/125; A61B 90/70;
(Continued)

(56) References Cited

U.S. PATENT DOCUMENTS 4,862,872 A 9/1989 Yabe et al.
2006/0269442 A1* 11/2006 Nguyen ................. A61B 1/125
422/28
(Continued)

FOREIGN PATENT DOCUMENTS

CN 103269638 A 8/2013
EP 0084342 A2 7/1983
(Continued)

OTHER PUBLICATIONS

International Search Report dated Jul. 4, 2017 issued in PCT/JP2017/014312.

*Primary Examiner* — Timothy C Cleveland
(74) *Attorney, Agent, or Firm* — Scully, Scott, Murphy & Presser, P.C.

(57) ABSTRACT

An endoscope reprocessing tool includes: a connection portion configured to be connected with a fluid outlet provided on a bottom face of a reprocessing basin of an endoscope reprocessor; a direction changing portion configured to change a flow direction of fluid discharged from the fluid outlet from a direction against a gravity direction to a direction crossing the gravity direction; a discharge portion configured to discharge the fluid direction-changed by the direction changing portion in the direction crossing the gravity direction; and a positioning portion configured to position a distal end portion of an endoscope so that the discharge portion and a recess portion provided on the distal end portion face each other.

15 Claims, 17 Drawing Sheets

(51) Int. Cl.
*A61L 2/26* (2006.01)
*A61B 90/70* (2016.01)

(52) U.S. Cl.
CPC ............... *A61B 90/70* (2016.02); *A61L 2/26* (2013.01); *A61B 2090/701* (2016.02); *A61L 2202/24* (2013.01)

(58) Field of Classification Search
CPC ....... A61B 2090/701; A61L 2/16; A61L 2/18; A61L 2/26; A61L 2202/15; A61L 2202/24
See application file for complete search history.

(56) References Cited

U.S. PATENT DOCUMENTS

| | | |
|---|---|---|
| 2013/0146108 A1 | 6/2013 | Suzuki et al. |
| 2017/0181611 A1 | 6/2017 | Yamaya |

FOREIGN PATENT DOCUMENTS

| | | |
|---|---|---|
| JP | S58-124428 A | 7/1983 |
| JP | S58-155834 A | 9/1983 |
| JP | S63-260523 A | 10/1988 |
| JP | 2006-246933 A | 9/2006 |
| JP | 2016-065771 A | 4/2016 |
| WO | WO 2015/107801 A1 | 7/2015 |
| WO | 2016/059920 A1 | 4/2016 |

\* cited by examiner

US 10,588,500 B2

ENDOSCOPE REPROCESSING TOOL

CROSS REFERENCE TO RELATED APPLICATION

This application is a continuation application of PCT/JP2017/014312 filed on Apr. 6, 2017 and claims benefit of Japanese Application No. 2016-087181 filed in Japan on Apr. 25, 2016, the entire contents of which are incorporated herein by this reference.

BACKGROUND OF INVENTION

1. Field of the Invention

The present invention relates to an endoscope reprocessing tool used for reprocessing of an endoscope.

2. Description of the Related Art

Some endoscopes used in a medical field are capable of causing a treatment instrument such as forceps and a puncture needle to project from a treatment instrument insertion opening that is open on a distal end portion of an insertion portion. For example, Japanese Patent Application Laid-Open Publication No. 2006-246933 discloses an endoscope provided with a treatment instrument raising base that guides a projection direction of a treatment instrument projecting from a treatment instrument insertion opening and causes the treatment instrument to swing. The treatment instrument raising base can be housed in a recess portion provided on a distal end portion so as not to be an obstruction at the time of causing the endoscope to move inside a subject.

For endoscopes used in the medical field, reprocessing such as cleaning processing and disinfection processing is performed after the endoscopes are used. The endoscope reprocessing can be automatically performed by an endoscope reprocessor.

SUMMARY OF THE INVENTION

An endoscope reprocessing tool according to an aspect of the present invention includes: a connection portion configured to be connected with a fluid outlet provided on a bottom face of a reprocessing basin of an endoscope reprocessor; a direction changing portion configured to change a flow direction of fluid discharged from the fluid outlet from a direction against a gravity direction to a direction crossing the gravity direction; a discharge portion configured to discharge the fluid direction-changed by the direction changing portion in the direction crossing the gravity direction; and a positioning portion configured to position a distal end portion of an endoscope so that the discharge portion and a recess portion provided on the distal end portion of the endoscope face each other.

Further, an endoscope reprocessing tool according to another aspect of the present invention includes: a connection portion configured to be connected with a nozzle provided on a bottom face of a reprocessing basin of an endoscope reprocessor and configured to discharge fluid in a direction crossing a gravity direction; and a positioning portion configured to position a distal end portion of an endoscope so that the nozzle and a recess portion provided on the distal end portion of the endoscope face each other.

DETAILED DESCRIPTION OF THE PREFERRED EMBODIMENT(S)

Figure 1:
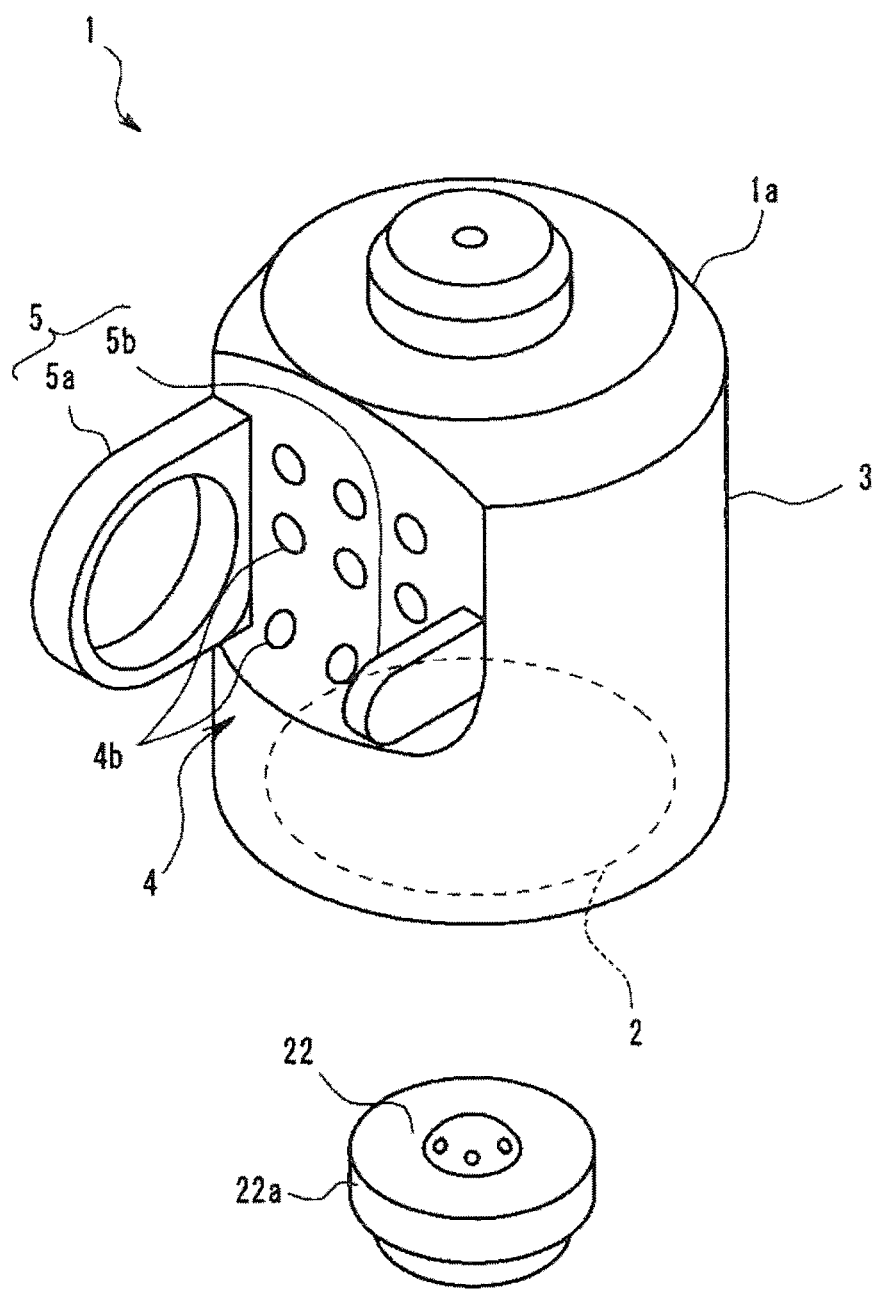
FIG. 1 is a perspective view of an endoscope reprocessing tool of a first embodiment seen from above.

Preferred embodiments of the present invention will be described below with reference to drawings. Note that, on each of drawings used in the description below, a reduced scale of each component is caused to be different so that the component is in a size recognizable on the drawing, and the present invention is not limited only to the number of components, shapes of the components, a ratio among the components, and a relative positional relationship among the respective components illustrated on the drawings.

Note that, in the description below, "above" or "upward" refers to a position farther from the ground relative to a comparison target, and "below" or "downward" refers to a position closer to the ground relative to the comparison target. Further, "upper" or "lower" in the description below indicates a height relationship along a gravity direction.

First Embodiment

Figure 2:
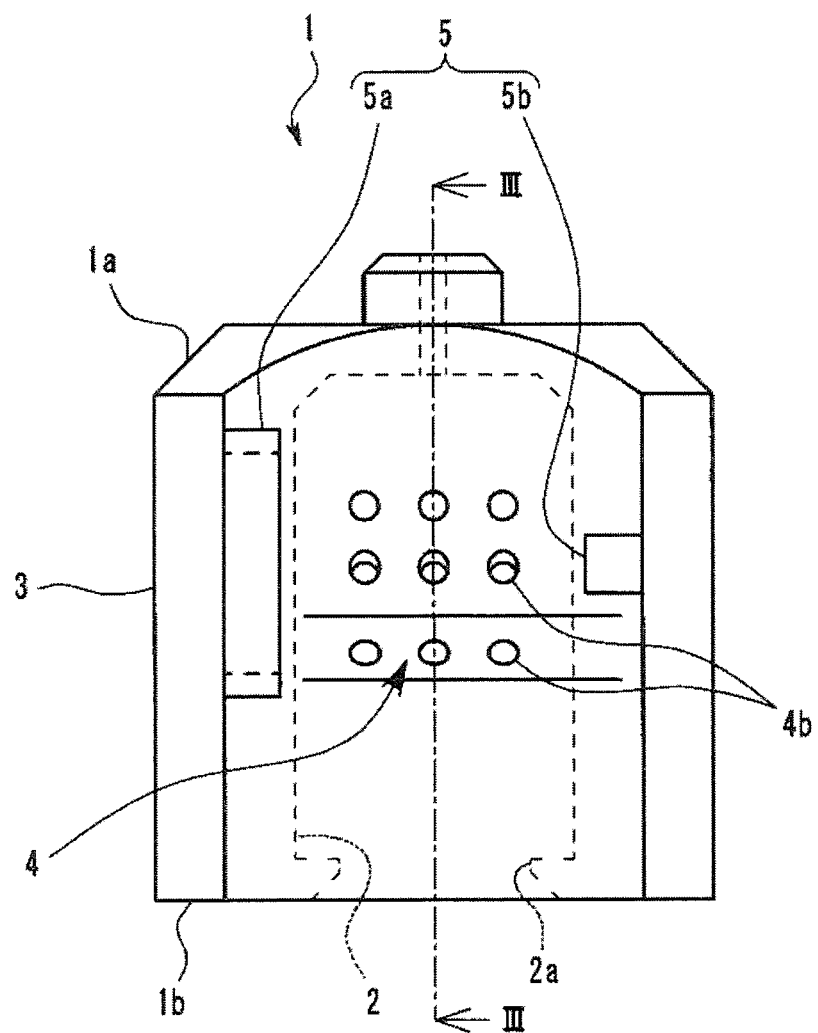
FIG. 2 is a diagram of the endoscope reprocessing tool of the first embodiment seen from a direction facing a discharge portion.
Figure 3:
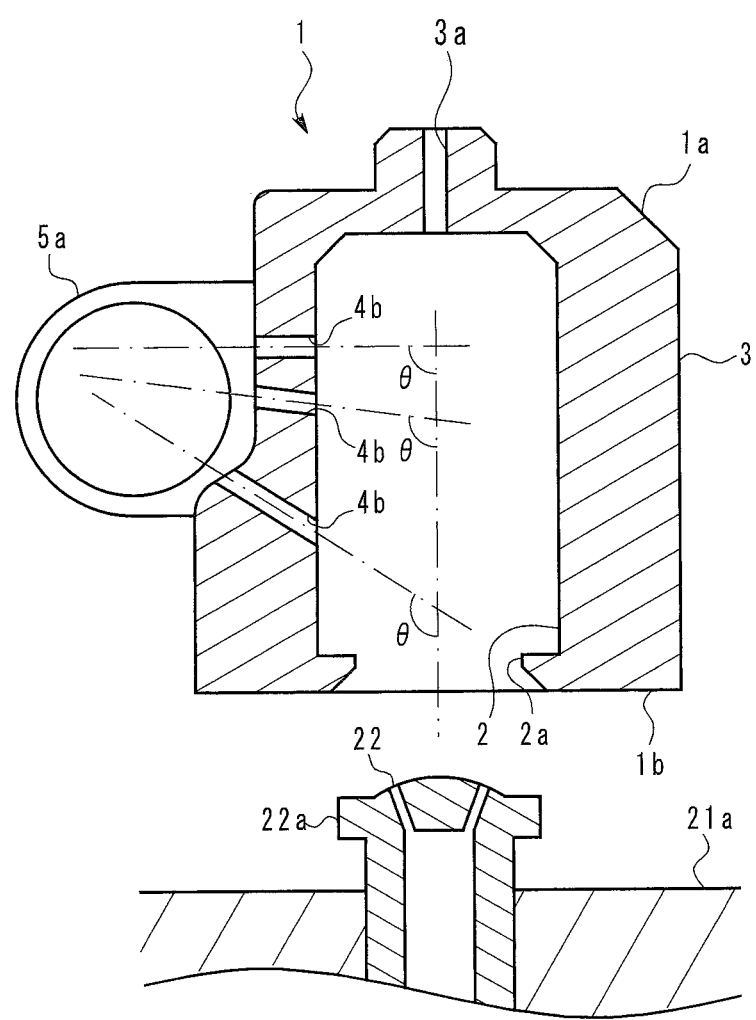
FIG. 3 is a diagram of a III-III cross-section of FIG. 2.

An example of embodiments of the present invention will be described below. An endoscope reprocessing tool 1 of the present embodiment shown in FIGS. 1 to 3 is used together with an endoscope reprocessor 20 that is an apparatus for performing reprocessing for an endoscope.

The reprocessing stated here is not especially limited but may be any of rinse processing with water, cleaning processing for removing soils such as organic matters, disinfection processing for disabling predetermined microorganisms, sterilization processing for causing all microorganisms to be excluded or killed and a combination of the above.

Figure 4:
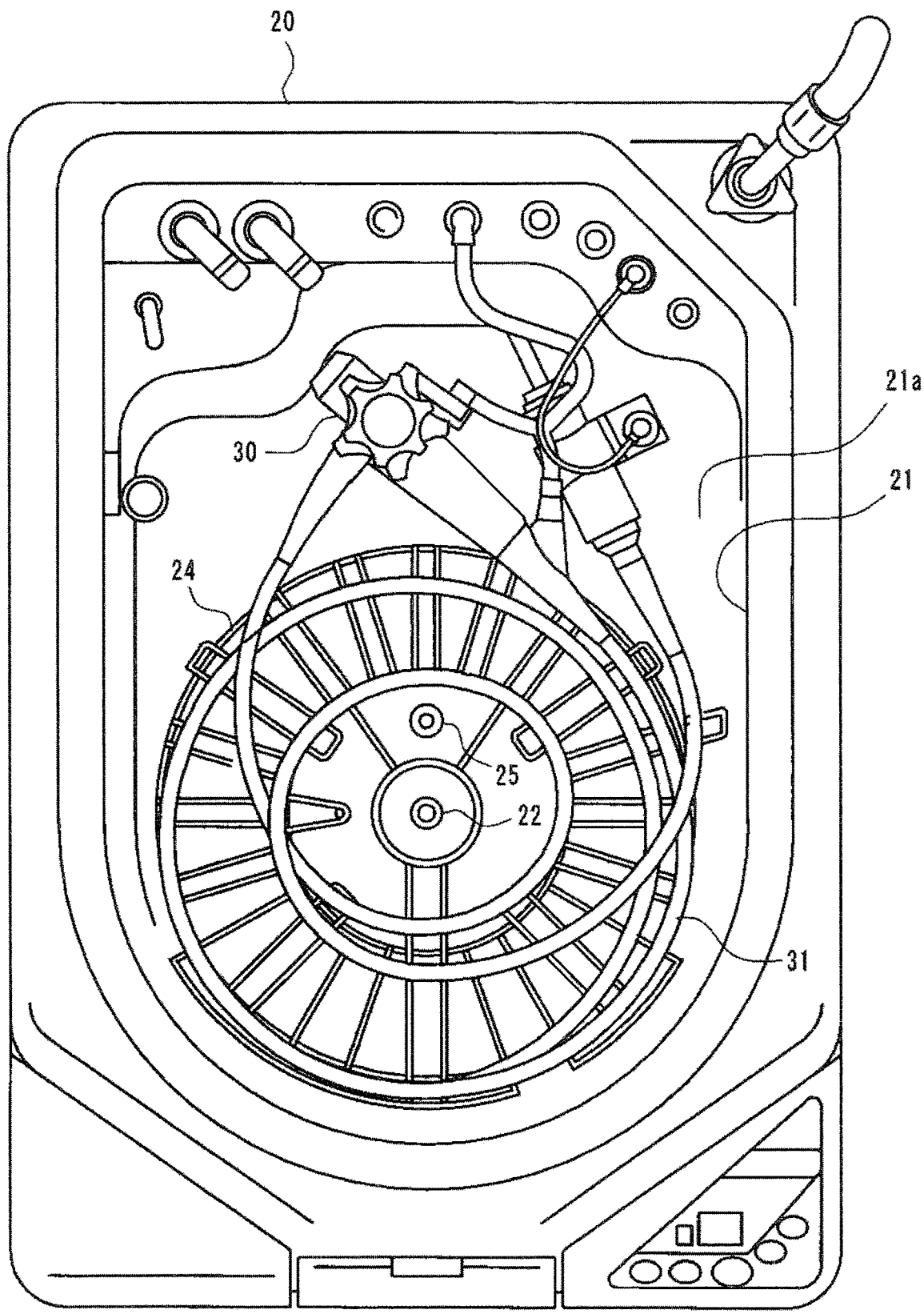
FIG. 4 is a diagram of a reprocessing basin of an endoscope reprocessor seen from above.

As shown in FIG. 4, the endoscope reprocessor 20 is provided with a reprocessing basin 21 configured to accommodate an endoscope 30. The endoscope reprocessor 20 has a configuration in which liquid such as cleaning solution, disinfection solution, sterilization solution, water or drying solution is introduced into the reprocessing basin 21, and performs reprocessing for the endoscope 30 arranged in the reprocessing basin 21. The reprocessing basin 21 is open upward, and the opening of the reprocessing basin 21 is provided with a cover 23 configured to open/close the opening though the cover 23 is not shown in FIG. 4.

A fluid outlet 22 is arranged on a bottom face 21a of the reprocessing basin 21. Fluid is discharged from the fluid outlet 22 into the reprocessing basin 21 in a direction against the gravity direction or in a direction crossing the gravity direction. The direction against the gravity direction stated here is not limited only to a direction vertically upward from the ground (a horizontal plane) but includes a direction obliquely upward from the ground. That is, the fluid outlet 22 is connected with a pump provided in the endoscope reprocessor 20, which is not shown, and fluid is discharged from the bottom face 21a of the reprocessing basin 21 by the pump operating. The fluid discharged from the fluid outlet 22 is fluid used for reprocessing and is cleaning solution, disinfection solution, sterilization solution, water, drying solution or the like.

Though the cleaning solution is not especially limited, for example, surfactant is given. Though the disinfection solution or the sterilization solution is not especially limited, for example, aqueous peracetic acid solution, aqueous glutaraldehyde solution, aqueous ortho-phthalaldehyde solution, highly acid electrolyte, alcohol or aqueous sodium hypochlorite solution is given. Though the drying solution is not especially limited, for example, alcohol or acetone is given.

The fluid outlet 22 is a cleaning case attaching port for attaching/detaching a cleaning case as an example in the present embodiment. The cleaning case is a container-like member for internally accommodating parts to be reprocessed, such as aaccessories of the endoscope 30, in the reprocessing basin 21. In a case where the cleaning case is fitted to the fluid outlet 22 that is a cleaning case attaching port, the cleaning case is provided with an opening for guiding fluid discharged from the fluid outlet 21 inside and an opening for guiding internal fluid outside. By fitting the cleaning case in which parts are accommodated to the fluid outlet 22 and executing reprocessing for the endoscope 30, fluid is introduced into the cleaning case, and reprocessing for the accommodated parts is performed. Though the cleaning case is not especially limited, for example, an endoscope accessory case 61 of Japanese Patent Application No. 2016-065771 is given.

As shown in FIG. 3, the fluid outlet 22 of the present embodiment is a nozzle with a cylindrical outer shape that is provided projecting upward from the bottom face 21a of the reprocessing basin 21. On an outer circumferential surface of the fluid outlet 22, a flange 22a with which a first detachable portion 2a of the endoscope reprocessing tool 1 described later is to be engaged is formed.

Note that the fluid outlet 22 is not limited to the configuration in which a cleaning case is directly attached to/detached from the fluid outlet 22. For example, the fluid outlet 22 may be an accessory cleaning nozzle attaching port which an accessory cleaning nozzle can be attached to/detached from, the accessory cleaning nozzle being for discharging fluid toward a side face of a cleaning case arranged away from the fluid.

Further, for example, the fluid outlet 22 may be a top surface cleaning nozzle that discharges fluid toward an internal surface of the cover 23 arranged at the top of the reprocessing basin 21 or may be a top surface cleaning nozzle attaching port which the top surface cleaning nozzle can be attached to/detached from.

Since a configuration of the endoscope reprocessor 20 is well known, detailed description will be omitted.

The endoscope reprocessing tool 1 is provided with a connection portion 2, a direction changing portion 3, a discharge portion 4 and a positioning portion 5.

The endoscope reprocessing tool 1 of the present embodiment is provided with a dome-shaped body portion 1a covering an upper part of the fluid outlet 22 projecting from the bottom face 21a of the reprocessing basin 21 as an example. That is, space is provided inside the body portion 1a.

The connection portion 2 is connected with the fluid outlet 22 provided on the bottom face 21a of the reprocessing basin 21 of the endoscope reprocessor 20. The connection portion 2 holds the body portion 1a at a position where the direction changing portion 3 of the endoscope reprocessing tool 1, which is described later, and the fluid outlet 22 communicate with each other inside the reprocessing basin 21. Therefore, when the connection portion 2 is connected with the fluid outlet 22, fluid discharged from the fluid outlet 22 flows into the direction changing portion 3 through the connection portion 2.

More specifically, the connection portion 2 of the present embodiment is a hole that is provided in an outer surface of the body portion 1a and into which the fluid outlet 22 projecting from the bottom face 21a of the reprocessing basin 21 can be inserted. The connection portion 2 of the present embodiment is provided with the first detachable portion 2a in a claw shape projecting from an inner circumferential surface toward the inside in a diameter direction. A distal end of the first detachable portion 2a projects to an inner side of an outer diameter of the flange 22a that projects from the outer circumference surface of the fluid outlet 22 in the diameter direction. Further, if the fluid outlet 22 is inserted into the connection portion 2 with predetermined or more strength of force, the first detachable portion 2a elastically deforms to allow passage of the flange 22a.

Figure 6:
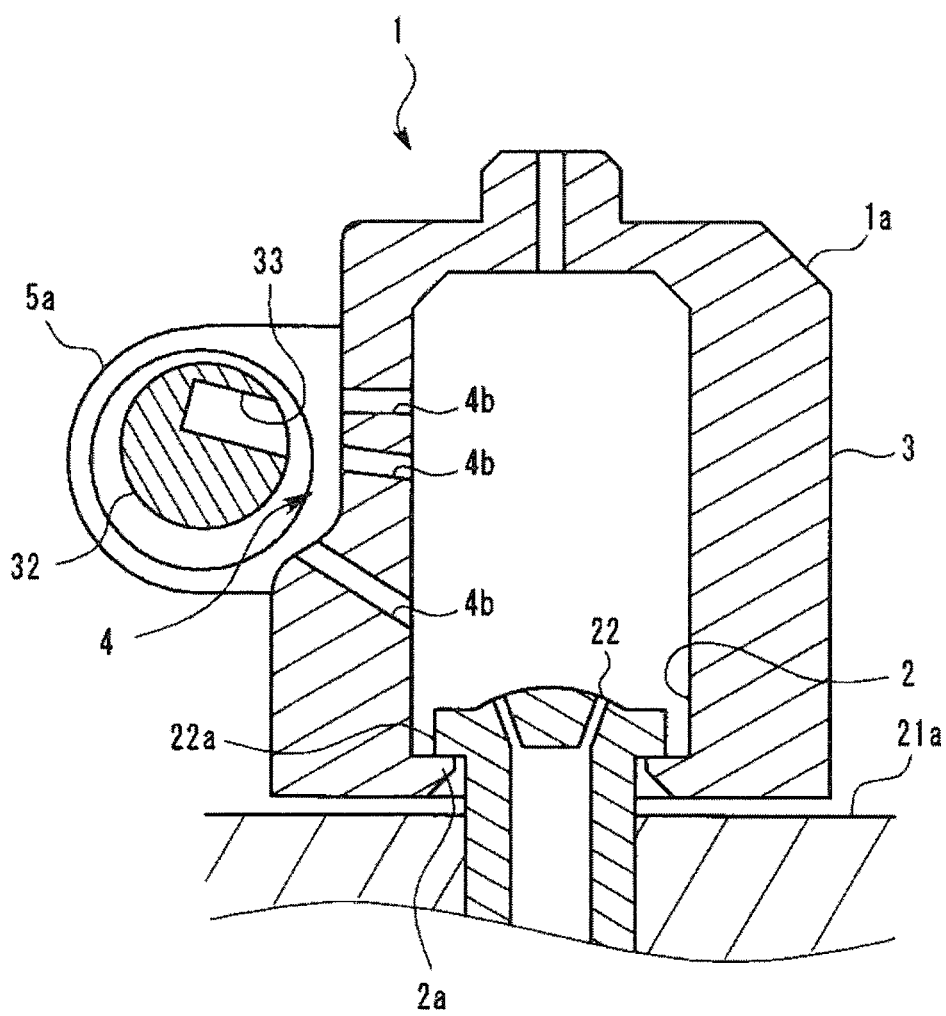
FIG. 6 is a diagram showing a state in which a connection portion of the endoscope reprocessing tool is connected with a fluid outlet, and a distal end portion of an insertion portion of an endoscope is positioned by a positioning portion on the cross section of FIG. 3.

Therefore, when the connection portion 2 is pressed to the fluid outlet 22 from above, the flange 22a passes through the first detachable portion 2a and advances in the connection portion 2 up to a position where the flange 22a is above the first detachable portion 2a as shown in FIG. 6. When force lifting up the connection portion 2 upward is applied in the state shown in FIG. 6, the first detachable portion 2a is engaged with the flange 22a, and reaction force is caused. Therefore, in the state shown in FIG. 6, the endoscope reprocessing tool 1 is held at a predetermined position by the connection portion 2.

Further, when the strength of the force lifting up the connection portion 2 upward in the state shown in FIG. 6 becomes a predetermined strength or more, the first detachable portion 2a elastically deforms and allows passage of the flange 22a, and, therefore, the connection portion 2 and the fluid outlet 22 are separated. Thus, the connection portion 2 has the configuration of enabling the endoscope reprocessing tool 1 to be attached to/detached from the fluid outlet 22. Note that, though a face of the first detachable portion 2a to be engaged with the flange 22a is flat in the shown embodiment, the face may be provided with unevenness such as a plurality of projections and grooves. By providing the unevenness on the face to be engaged with the flange 22a, a frequency of contact between the first detachable portion 2a and the flange 22a, and fluid used for reprocessing can be increased in a state in which the connection portion 2 is connected with the fluid outlet 22.

In description below, a face on which the connection portion 2 of the body portion 1a opens is assumed to be a lower face 1b. The lower face 1b is a face facing downward in the state in which the connection portion 2 is connected with the fluid outlet 22. Note that, though the lower face 1b of the body portion 1a is flat in the shown embodiment, the lower face may be provided with unevenness such as a plurality of projections and grooves. By providing the unevenness on the lower face 1b facing the bottom face 21a of the reprocessing basin 21, a frequency of contact between the lower face and the bottom face 21a, and fluid used for reprocessing can be increased in the state in which the connection portion 2 is connected with the fluid outlet 22.

The direction changing portion 3 changes a flow direction of fluid discharged from the fluid outlet 22 to a direction crossing the gravity direction in the state in which the connection portion 2 is connected with the fluid outlet 22. The direction changing portion 3 is space formed in the body portion 1a as described before and communicates with the connection portion 2. Further, the direction changing portion 3 communicates with the discharge portion 4. The discharge portion 4 discharges the fluid the direction of which has been changed by the direction changing portion 3, in the direction crossing the gravity direction in the state in which the connection portion 2 is connected with the fluid outlet 22. As stated before, the discharge direction of fluid discharged from the fluid outlet 22 is not limited to the direction vertically upward from the ground but includes the direction obliquely upward from the ground. When fluid is led in a direction obliquely upward from the ground, from the fluid outlet 22, the direction changing portion 3 causes the flow direction of the fluid to be a direction the angle of which formed with the gravity direction is smaller.

The direction changing portion 3 of the present embodiment is arranged above the connection portion 2 when the connection portion 2 is connected with the fluid outlet 22, and has a wall surface covering the upper part of the fluid outlet 22. The shown direction changing portion 3 of the present embodiment is in a closed cylindrical shape in which one end communicates with the connection portion 2, and the other end is closed. Further, the direction changing portion 3 may be provided with a top surface cleaning hole 3a for discharging fluid toward the internal surface of the cover 23 arranged above the reprocessing basin 21. Note that the shape of the direction changing portion 3 is not limited to the shape in the present embodiment. The direction changing portion 3 may be, for example, in a spherical shape, a hemispherical shape or a box shape or may be a slope facing the discharge portion 4.

The discharge portion 4 of the present embodiment is provided with a plurality of holes 4b penetrating the direction changing portion 3 from the outer surface to the internal space. In the present embodiment, the discharge portion 4 is provided on a face to be a side face of the body portion 1a when the connection portion 2 is connected with the fluid outlet 22 as an example.

The plurality of holes 4b are formed in the discharge portion 4 along a line crossing the gravity direction at a predetermined angle, which will be described in detail later.

Therefore, the discharge portion 4 discharges fluid discharged from the fluid outlet 22 to a direction crossing the gravity direction from a side face of the direction changing portion 3 in the state in which the connection portion 2 is connected with the fluid outlet 22. Note that, though the plurality of holes 4b have a shape of linearly penetrating the direction changing portion 3 from the outer surface to the internal space in shown present embodiment, the plurality of holes 4b may be in a shape of being bent midway or may be in a nozzle shape projecting from the outer surface. Further, the discharge portion 4 may be provided with slits instead of a plurality of holes or may be provided with both holes and slits.

The plurality of holes 4b are arrayed in a substantially horizontal direction when the connection portion 2 is connected with the fluid outlet 22. At least one row of the plurality of holes 4b is provided. A plurality of rows of a plurality of holes 4b may be provided in a vertical direction. In the shown present embodiment, three rows each of which is constituted by a plurality of holes 4b arranged in a horizontal direction are provided in the vertical direction as an example.

In the case of providing a plurality of rows of a plurality of holes 4b in the vertical direction, it is preferred that two or more rows are included, on which angles of the individual holes 4b are set so that a crossing angle θ between a fluid discharge direction and the gravity direction becomes smaller for a row farther from a gravity source (an upper row).

Here, the crossing angle θ between the fluid discharge direction and the gravity direction is 90 degrees when the fluid discharge direction is horizontal, and the value increases when the fluid discharge direction is above horizontality. That is, the crossing angle θ between the fluid discharge direction and the gravity direction takes a value larger than 90 degrees and smaller than 180 degrees when the fluid discharge direction is at an elevation angle and takes a value smaller than 90 degrees and larger than 0 degree when the fluid discharge direction is at a depression angle.

By setting fluid discharge directions of the plurality of holes 4b so that the crossing angle θ between a fluid discharge direction and the gravity direction becomes smaller for an upper row as described above, fluid discharged from each individual row flows crossing fluid discharged from the other rows on a plane parallel to the gravity direction shown in FIG. 3. However, among the rows, above the rows or below the rows, holes with a crossing angle θ larger than the crossing angles θ of the lower rows or holes with a crossing angle θ smaller than the crossing angles θ of the upper rows may be arranged. For example, referring to FIG. 3 as an example, holes with a crossing angle θ of 90 degrees may be provided further below the lowest holes 4b shown in FIG. 3. Fluid discharged from the holes is discharged toward a part other than a recess portion 33 provided on a distal end portion 32 of an insertion portion 31 of the endoscope 30, for example, an outer surface of the distal end portion 32.

The positioning portion 5 positions the distal end portion 32 so that the discharge portion 4 and the recess portion 33 provided on the distal end portion 32 of the insertion portion 31 of the endoscope 30 face each other when the connection portion 2 is connected with the fluid outlet 22.

Note that, in the present embodiment, the recess portion 33 provided on the distal end portion 32 of the insertion portion 31 of the endoscope 30 is a recess portion in which a treatment instrument swinging portion is arranged as an example. When the insertion portion 32 of the endoscope 30 is wound as shown in FIG. 5 in the reprocessing basin 21 of the endoscope reprocessor 20, the recess portion 33 is open in a direction crossing the gravity direction.

Figure 5:
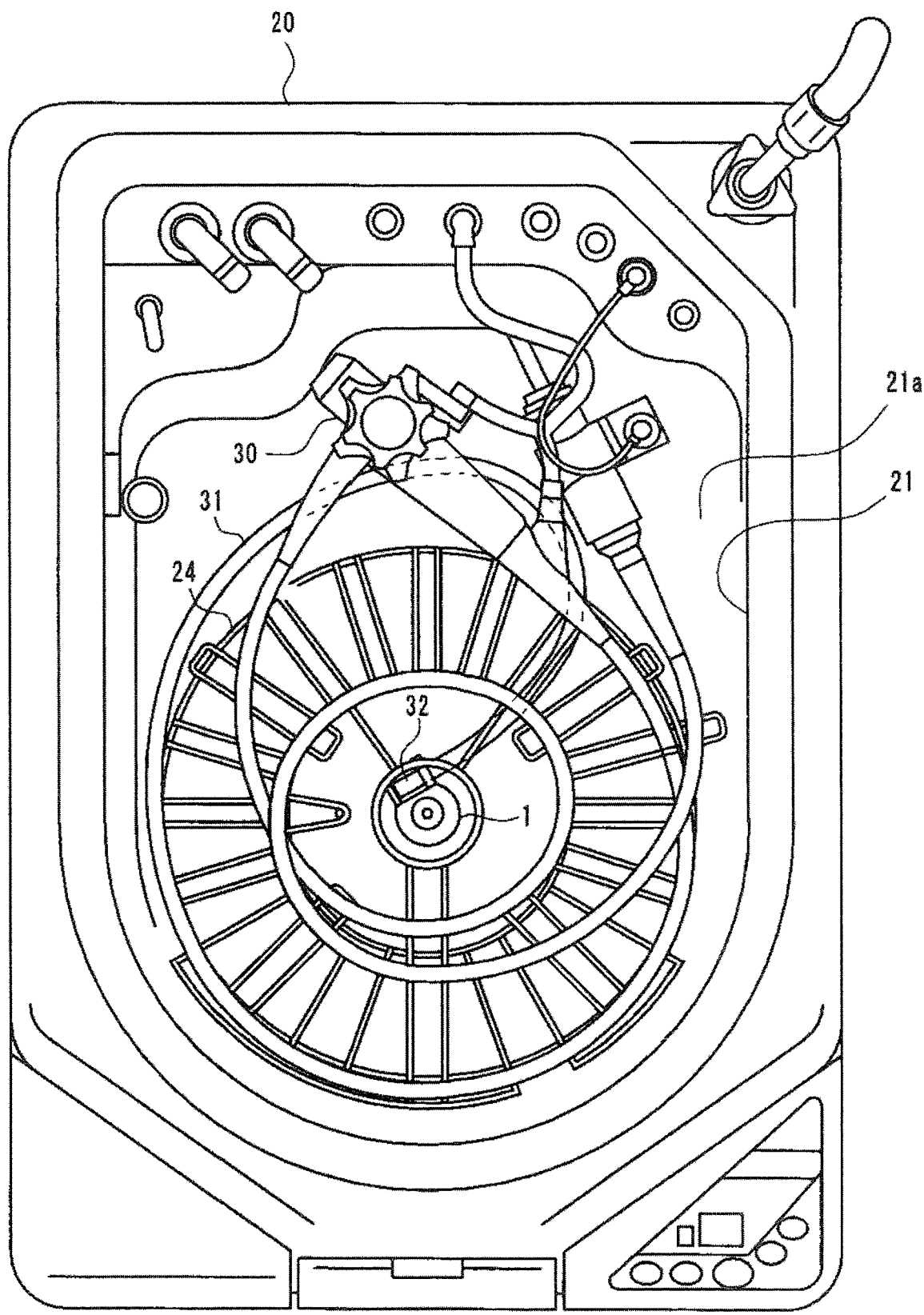
FIG. 5 is a diagram showing a state in which the endoscope reprocessing tool is arranged in the reprocessing basin of the endoscope reprocessor.
Figure 7:
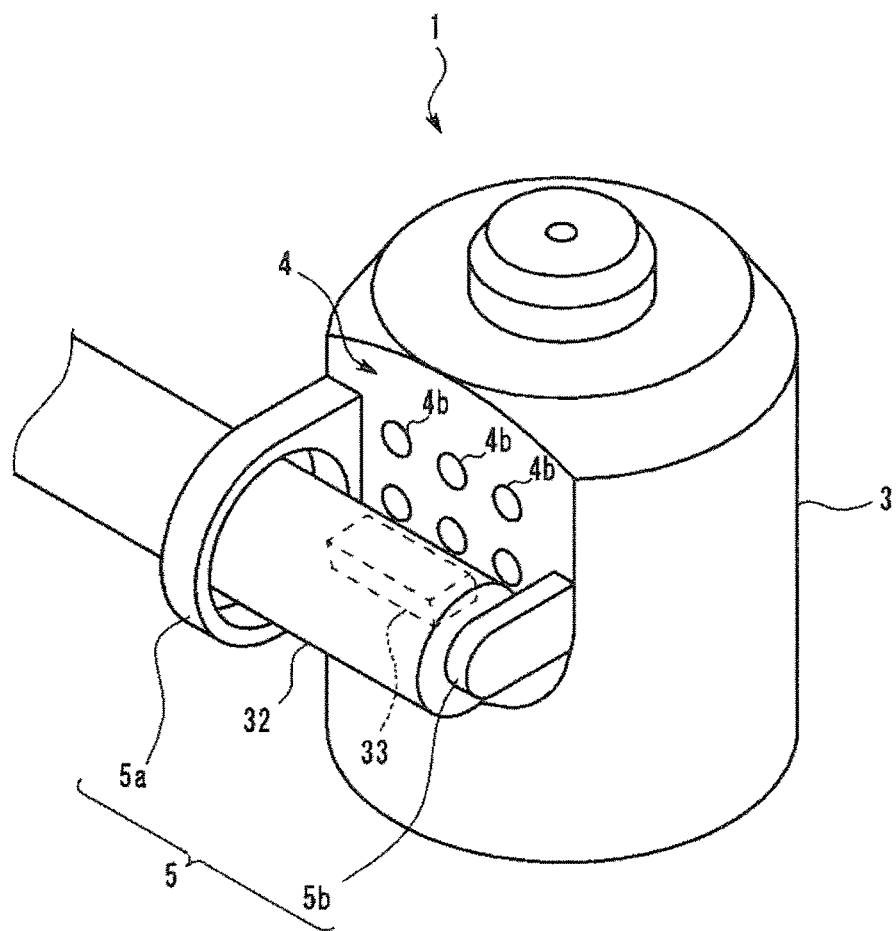
FIG. 7 is a diagram showing the state in which the connection portion of the endoscope reprocessing tool is connected with the fluid outlet, and the distal end portion of the insertion portion of the endoscope is positioned by the positioning portion on the perspective view of FIG. 1.

FIGS. 5, 6 and 7 show the state in which the connection portion 2 of the endoscope reprocessing tool 1 is connected with the fluid outlet 22 and show a state the distal end portion 32 of the insertion portion 31 of the endoscope 30 is positioned by the positioning portion 5.

The positioning portion 5 of the present embodiment has a holding portion 5a surrounding a circumference of the distal end portion 32 of the insertion portion 31 of the endoscope 30 and an abutting portion 5b against which the distal end portion 32 inserted in the holding portion 5a abuts.

The holding portion 5a, as shown in FIG. 6, surrounds the circumference of the distal end portion 32 of the insertion portion 31 when the distal end portion 32 is seen from an insertion direction. Here, the insertion direction of the distal end portion 32 refers to a longitudinal direction of the insertion portion 31 that is in an elongated shape.

The holding portion 5a, by surrounding the circumference of the distal end portion 32, performs vertical-direction positioning of the distal end portion 32 relative to the discharge portion 4 and positioning for a distance of separation of the distal end portion 32 from the discharge portion 4 in the horizontal direction in the case where the connection portion 2 is connected with the fluid outlet 22. It is preferred that the separation distance between the distal end portion 32 and the discharge portion 4 is short.

Note that, in the shown present embodiment, the holding portion 5a has a through hole drilled along an axis that is horizontal when the connection portion 2 is connected with the fluid outlet 22, and the through hole has an inner diameter larger than an outer diameter of the distal end portion 32. In the present embodiment, the vertical-direction positioning and separation-distance positioning of the distal end portion 32 relative to the discharge portion 4 are performed by inserting the distal end portion 32 into the through hole.

Note that, though the holding portion 5a is provided with a circular through hole in the shown present embodiment, the through hole may be in another shape, for example, a rectangular shape. Further, the shape of the holding portion 5a is not limited to the shape surrounding the whole circumference of the distal end portion 32 as in the present embodiment but may be any shape that enables the vertical-direction positioning and the separation distance positioning of the distal end portion 32 relative to the discharge portion 4. For example, the holding portion 5a may be in a shape of being provided with a pair of rod-shaped members arranged above and below the distal end portion 32 so as to sandwich the distal end portion 32 between the discharge portion 4 and the pair of rod-shaped members. Further, the holding portion 5a may be in a C shape.

The abutting portion 5b comes into contact with an end portion of the distal end portion 32 when the distal end portion 32 is inserted into the through hole of the holding portion 5a by a predetermined length and performs insertion-direction positioning of the distal end portion 32 relative to the discharge portion 4.

Note that, though the abutting portion 5b is a projection projecting from the outer surface of the direction changing portion 3 in the shown present embodiment, the shape of the abutting portion 5b is not limited to the shape in the present embodiment, and any shape that restricts positions of the distal end portion 32 and the discharge portion 4 inserted into the holding portion 5a is possible. For example, the abutting portion 5b may be a netlike member arranged at a predetermined distance from the holding portion 5a in the insertion direction.

As described above, the endoscope reprocessing tool 1 is provided with: the connection portion 2 to be connected with the fluid outlet 22 provided on the bottom face 21a of the reprocessing basin 21 of the endoscope reprocessor 20; the direction changing portion 3 configured to change a flow direction of fluid discharged from the fluid outlet 22, from the direction against the gravity direction to a direction crossing the gravity direction; the discharge portion 4 configured to discharge the fluid the direction of which has been changed by the direction changing portion 3 in a direction crossing the gravity direction; and the positioning portion 5 configured to perform positioning of the recess portion 33 provided on the distal end portion 32 of the insertion portion 31 of the endoscope 30 so that the recess portion 33 faces the discharge portion 4.

The fluid outlet 22 is a part configured to discharge fluid used for reprocessing when the endoscope reprocessor 20 executes reprocessing. Therefore, by using the endoscope reprocessing tool 1 of the present embodiment, it is possible to send fluid used for reprocessing into the recess portion 33 provided on the distal end portion 32 of the insertion portion 31 of the endoscope 30 at the time of executing reprocessing by the endoscope reprocessor 20 and focus on performing reprocessing in the recess portion 33.

Further, the discharge portion 4 of the endoscope reprocessing tool 1 of the present embodiment is provided with a row of plurality of holes 4b configured to discharge fluid, the plurality of holes 4b being arranged in the horizontal direction. That is, on the endoscope reprocessing tool 1 of the present embodiment, the plurality of holes 4b configured to discharge fluid are arranged in a direction along the insertion direction of the distal end portion 32 positioned by the positioning portion 5. The recess portion 33 provided on the distal end portion 32 of the insertion portion 31 of the endoscope 30 has an opening shape the longitudinal direction of which is the insertion direction. In the present embodiment, since fluid is discharged from the plurality of holes 4b arrayed along the longitudinal direction of the recess portion 33, the fluid can be sent to the whole inside of the recess portion 33 evenly.

Further, the discharge portion 4 of the endoscope reprocessing tool 1 of the present embodiment is configured by arranging a plurality of rows of plurality of holes 4b for discharging fluid that are arranged in the horizontal direction, in the vertical direction. For the rows of the plurality of holes 4b, angles of the individual holes 4b are set so that the crossing angle $\theta$ between a fluid discharge direction and the gravity direction becomes smaller for a row farther from the gravity source. Due to the insertion portion 31 being easily twisted because of a usage environment of the endoscope 30, and the like, variation occurs in a position where the recess portion 33 is open when the endoscope 30 is arranged in the reprocessing basin 21 in a rotation direction around a longitudinal axis of the distal end portion 32. However, according to the endoscope reprocessing tool 1 of the present embodiment, by causing the angles of the plurality of holes 4b arranged in the vertical direction to be different, it is possible to certainly send fluid into the recess portion 33 even if the opening direction of the recess portion 33 changes in the rotation direction around the longitudinal axis of the distal end portion 32.

Note that, though the connection portion 2 to be connected with the fluid outlet 22 is provided with the first detachable portion 2a configured to be engaged with the fluid outlet 22 to perform positioning of the endoscope reprocessing tool 1 relative to the fluid outlet 22 in the endoscope reprocessing tool 1 of the present embodiment described above, the configuration for performing positioning of the endoscope reprocessing tool 1 relative to the fluid outlet 22 may be provided at a position different from the connection portion 2.

Figure 8:
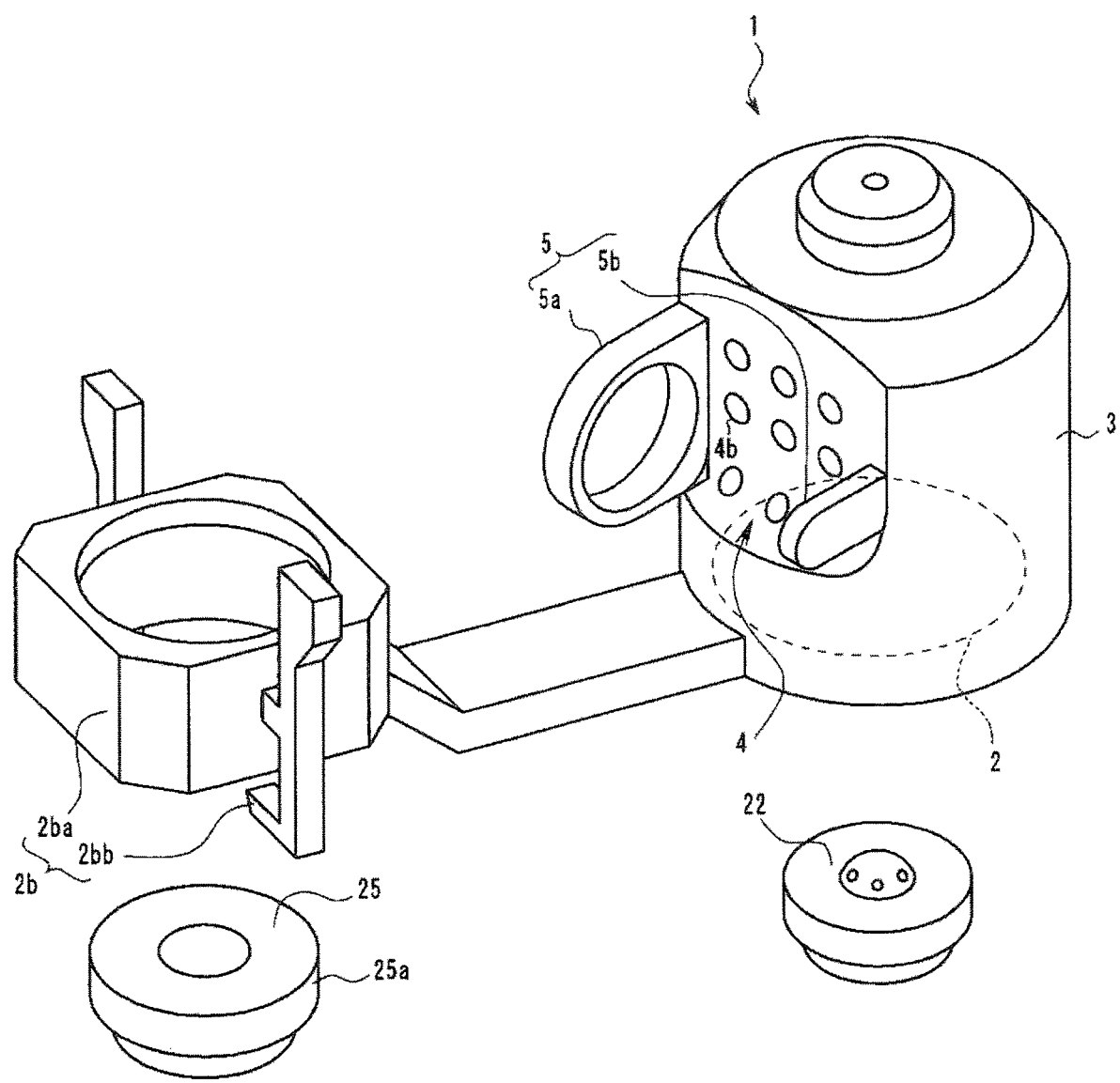
FIG. 8 is a diagram showing a first modification of the endoscope reprocessing tool of the first embodiment.

FIG. 8 shows a first modification of the endoscope reprocessing tool 1. The endoscope reprocessing tool 1 of the present modification has a second detachable portion 2b that is attached to/detached from a connector 25 provided on the bottom face 21a of the reprocessing basin 21 of the endoscope reprocessor 20. In the present embodiment, the second detachable portion 2b can be attached to/detached from the connector 25 as an example.

In the present embodiment, the connector 25 is a self-disinfecting connector for, at the time of disinfecting the inside of a water conduit for supplying water to the endoscope reprocessor 20, connecting a hose for connecting a disinfection solution nozzle for discharging disinfection solution, which is provided in the reprocessing basin 21, and the water conduit, as an example.

As shown in FIG. 4, the connector 25 is arranged adjoining the fluid outlet 22. Further, as shown in FIG. 8, the connector 25 is in a cylindrical shape projecting upward from a bottom face 21b of the reprocessing basin 21 and has a flange 25a projecting from an outer circumference portion in a diameter direction.

The second detachable portion 2b of the present modification is provided projecting from the outer surface of the direction changing portion 3. The second detachable portion 2b has a cylindrical portion 2ba into which the connector 25 can be inserted, and engaging claws 2bb configured to be engaged with the flange 25a in a state in which the connector 25 is inserted in the cylindrical portion 2ba. By the engaging claws 2bb with the flange 25a, a position of the second detachable portion 2b relative to the connector 25 is fixed. Then, in the present modification, by the second detachable portion 2b being fixed to the connector 25, the connection portion 2 of the endoscope reprocessing tool 1 is positioned at a position of being connected with the fluid outlet 22.

Figure 9:
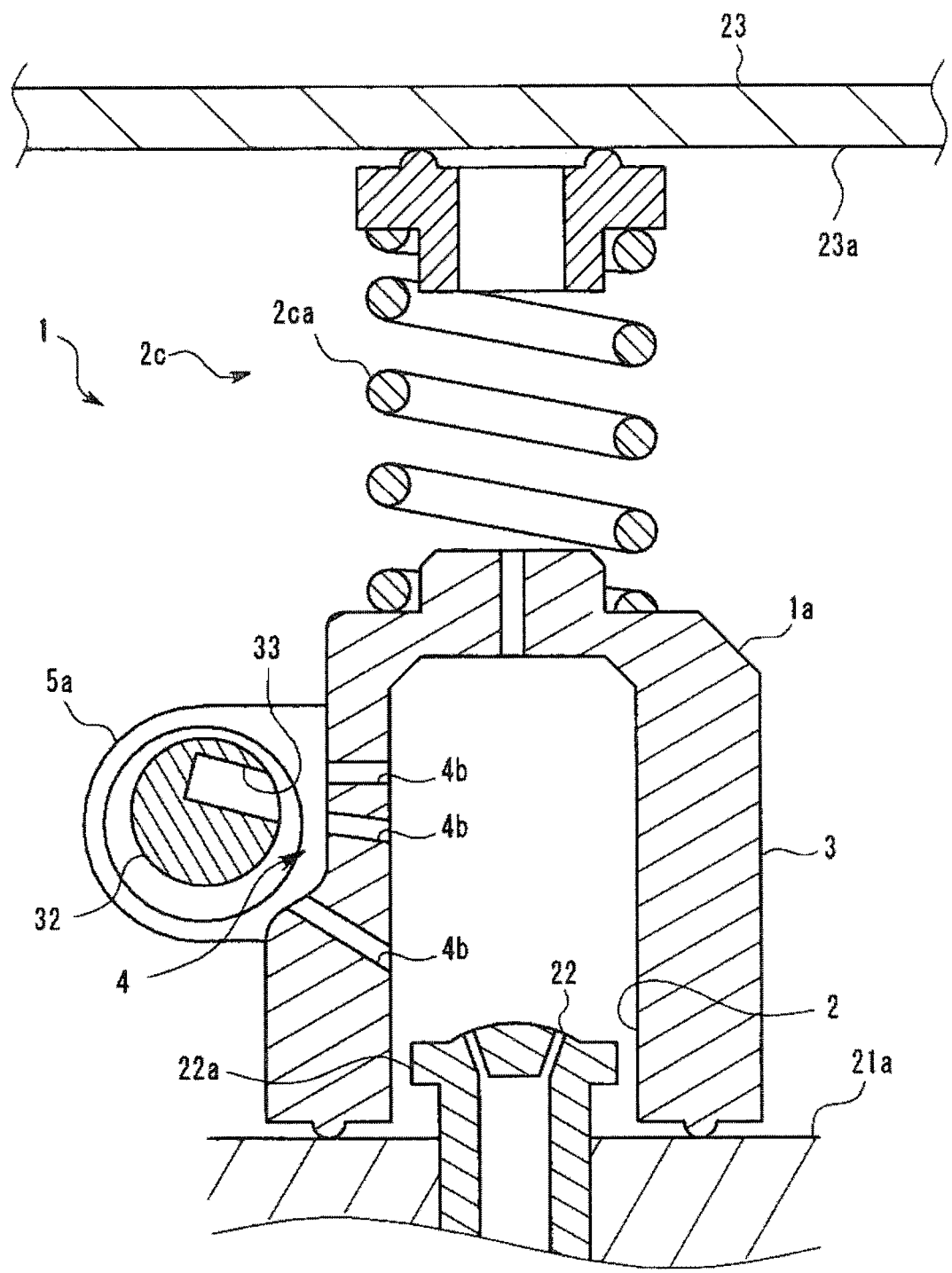
FIG. 9 is a diagram showing a second modification of the endoscope reprocessing tool of the first embodiment.

Next, a second modification of the endoscope reprocessing tool 1 is shown in FIG. 9. The endoscope reprocessing tool 1 of the present modification has a third detachable portion 2c.

The third detachable portion 2c is provided with an urging portion 2ca. The urging portion 2ca is a compression spring sandwiched between an internal surface 23a of the cover 23 arranged at the top of the reprocessing basin 21 and a top face of the outer surface of the direction changing portion 3. By being sandwiched between the cover 23 and the direction changing portion 3, the urging portion 2ca generates urging force pressing the direction changing portion 3 and the connection portion 2 to the bottom face 21a of the reprocessing basin 21. In the present modification, by the urging force generated by the urging portion 2ca, the connection portion 2 of the endoscope reprocessing tool 1 is positioned at the position of being connected with the fluid outlet 22.

Note that the urging portion 2ca is not limited to the form of a compression spring but may be a plate spring or may be in a form of being configured with an elastic member such as a rubber member.

Figure 10:
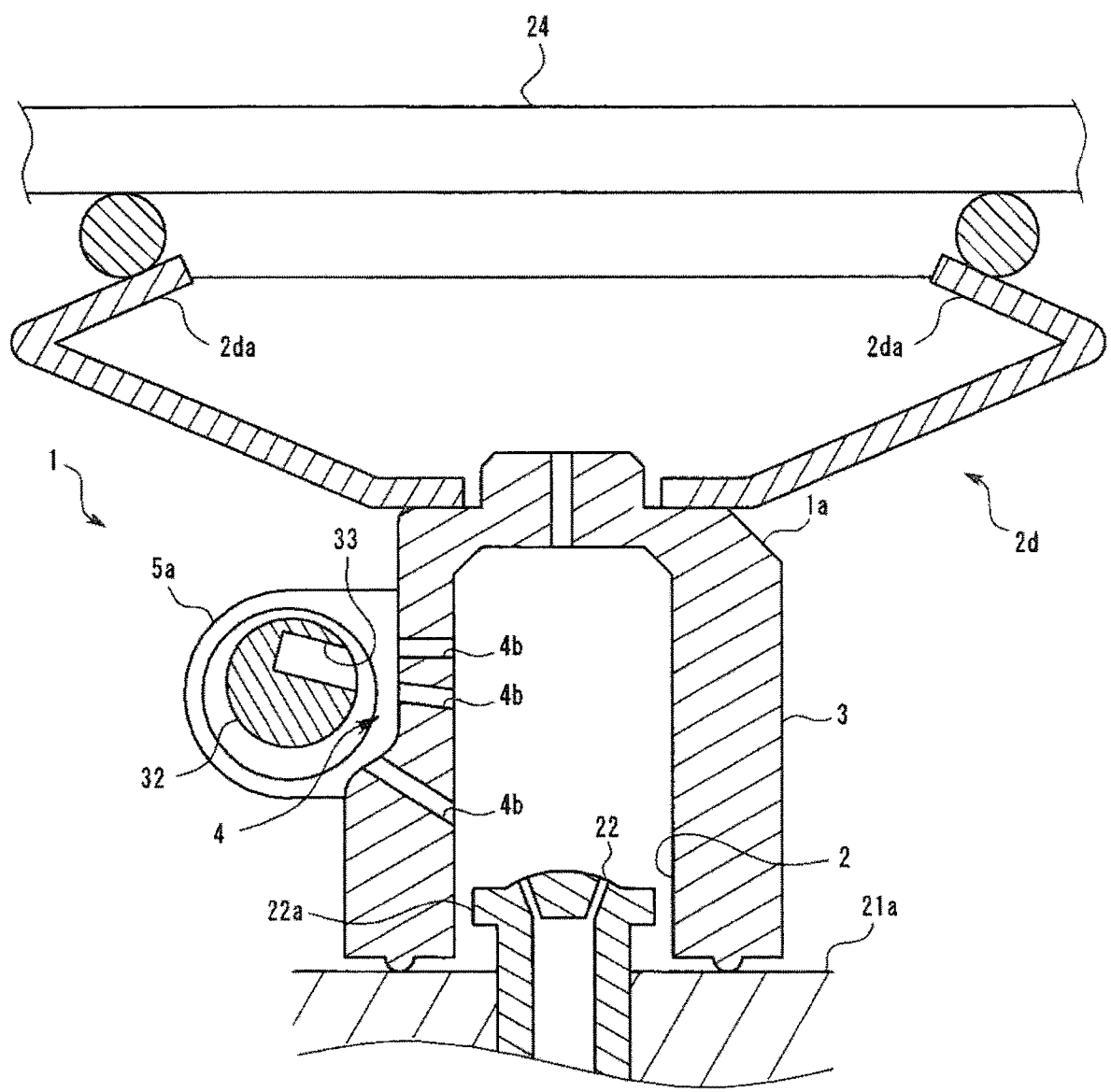
FIG. 10 is a diagram showing a third modification of the endoscope reprocessing tool of the first embodiment.

Next, a third modification of the endoscope reprocessing tool 1 is shown in FIG. 10. The endoscope reprocessing tool 1 of the present modification has a fourth detachable portion 2d.

The fourth detachable portion 2d is provided with an urging portion 2da. The urging portion 2da is a compression spring sandwiched between a retaining rack 24 arranged above the bottom face 21a of the reprocessing basin 21 and the top face of the outer surface of the direction changing portion 3. The retaining rack 24 is a netlike member holding the endoscope 30 at a position above and away from the bottom face 21a in the reprocessing basin 21.

The urging portion 2da is sandwiched between the retaining rack 24 and the direction changing portion 3 and generates urging force pressing the direction changing portion 3 and the connection portion 2 to the bottom face 21a of the reprocessing basin 21 by weights of the retaining rack 24 and the endoscope 30 held by the retaining rack 24. In the present modification, by the urging force generated by the urging portion 2da, the connection portion 2 of the endoscope reprocessing tool 1 is positioned at a position of being connected with the fluid outlet 22.

Note that the urging portion 2da is not limited to the form of a plate spring but may be a compression coil spring or may be in a form of being configured with an elastic member such as a rubber member.

Second Embodiment

Figure 11:
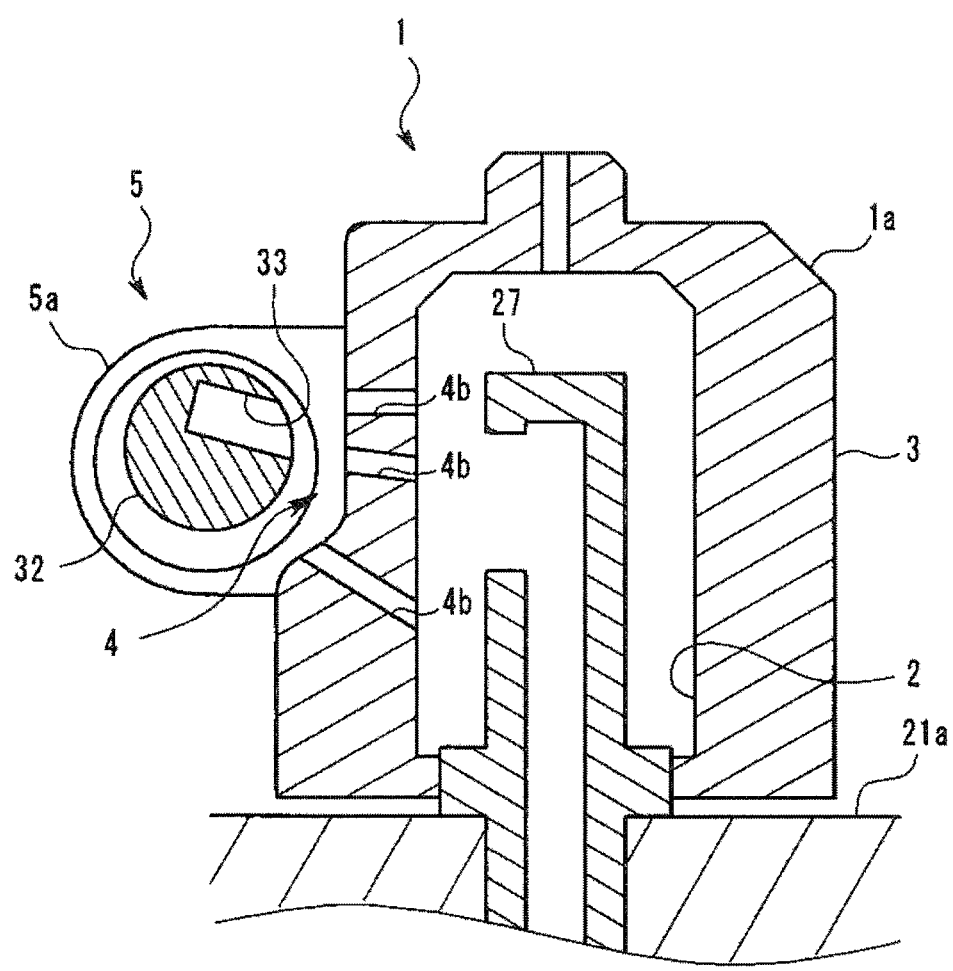
FIG. 11 is a diagram showing an endoscope reprocessing tool of a second embodiment.

A second embodiment of the present invention will be described below. Only points different from the first embodiment will be described below. Components similar to those of the first embodiment will be given the same reference numerals, and description of the components will be appropriately omitted. FIG. 11 shows an endoscope reprocessing tool 1 of the second embodiment.

The endoscope reprocessing tool 1 of the second embodiment is fitted to a nozzle 27 provided on the bottom face 21a of the reprocessing basin 21 of the endoscope reprocessor 20 and configured to discharge fluid in a direction crossing the gravity direction. Though the nozzle 27 is not especially limited, an accessory cleaning nozzle for discharging fluid toward a side face of a cleaning case arranged away is given. It is preferred that the cleaning case used in combination with the accessory cleaning nozzle is in a form enabling fluid to be introduced from a net or lattice side face.

The endoscope reprocessing tool 1 of the second embodiment includes the connection portion 2 to be connected with the nozzle 27 and the positioning portion 5 configured to position the distal end portion 32 of the insertion portion 31 of the endoscope 30. Furthermore, it is preferred that the endoscope reprocessing tool 1 of the second embodiment includes the discharge portion 4.

The connection portion 2, the positioning portion 5 and the discharge portion 4 of the endoscope reprocessing tool 1 of the second embodiment are similar to those of the endoscope reprocessing tool 1 of the first embodiment. As shown in FIG. 11, in the endoscope reprocessing tool of the second embodiment, the body portion 1a may be a shape covering the nozzle 27 or may be a shape exposing the nozzle 27.

Third Embodiment

Figure 12:
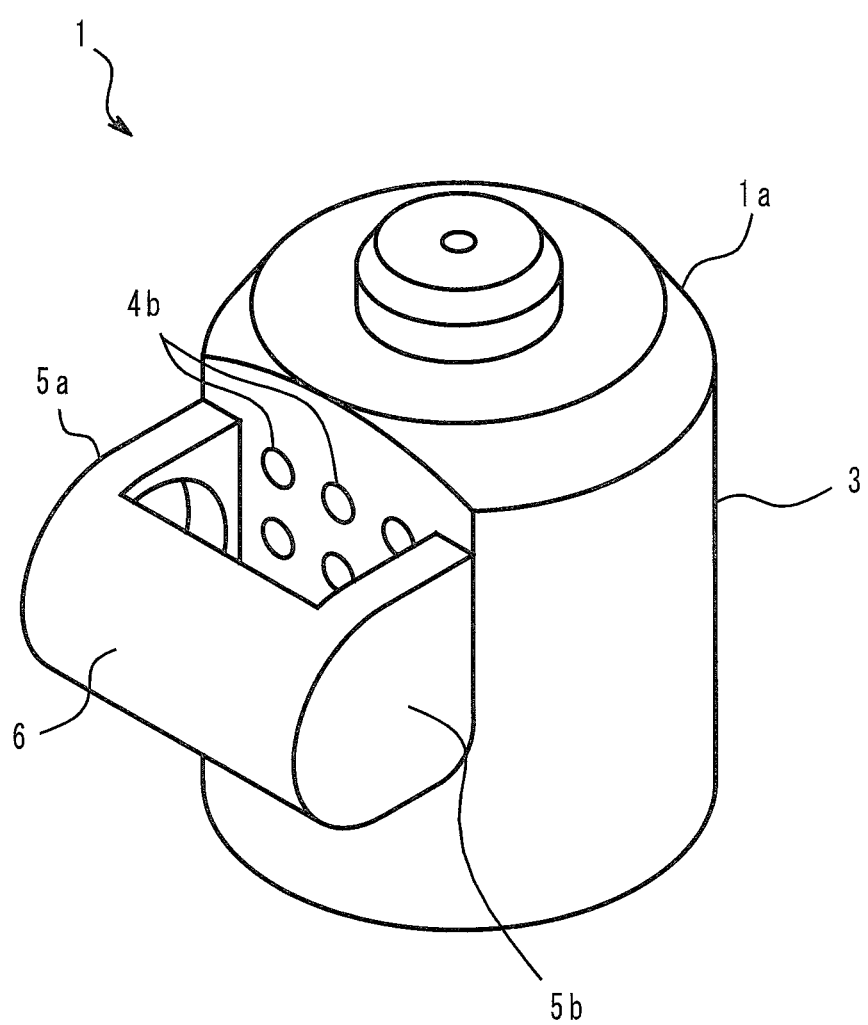
FIG. 12 is a perspective view of an endoscope reprocessing tool of a third embodiment seen from above.
Figure 13:
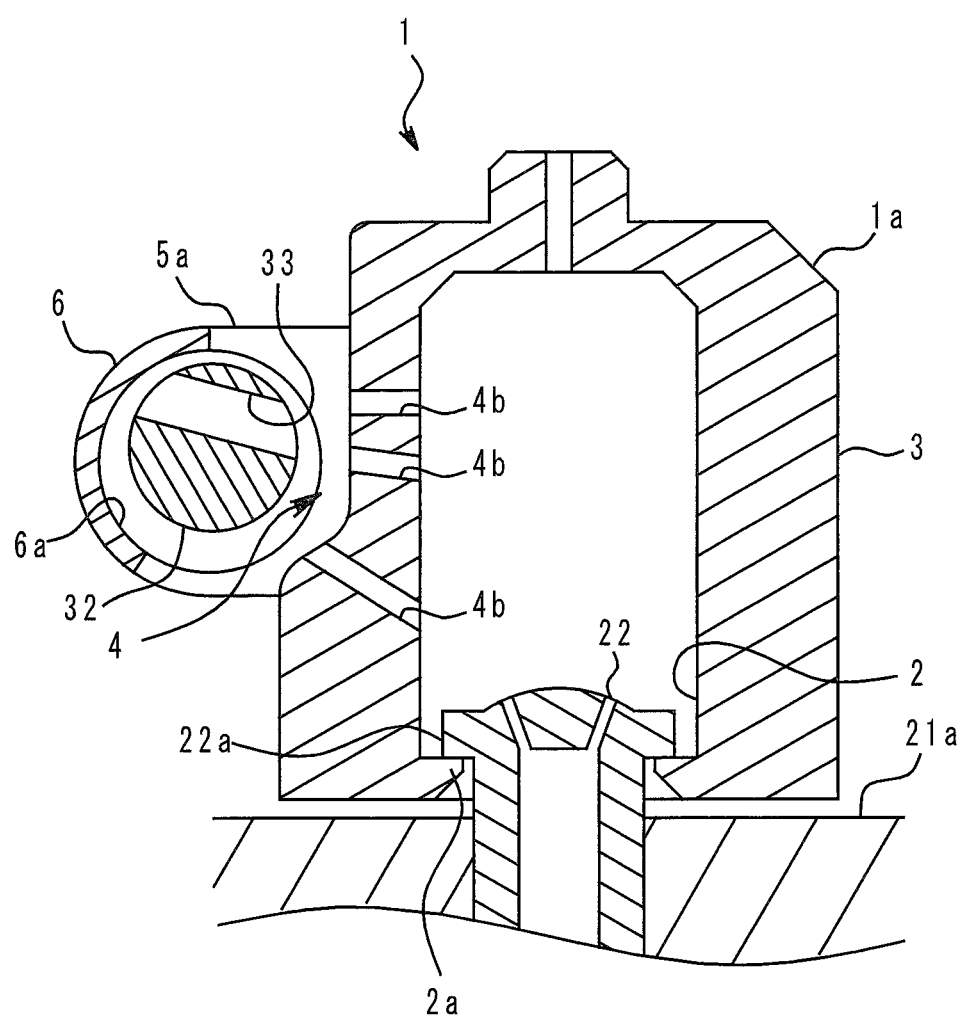
FIG. 13 is a cross-sectional view of the endoscope reprocessing tool of the third embodiment.

A third embodiment of the present invention will be described below. Only points different from the first embodiment will be described below. Components similar to those of the first embodiment will be given the same reference numerals, and description of the components will be appropriately omitted. FIGS. 12 and 13 show an endoscope reprocessing tool 1 of the third embodiment.

The endoscope reprocessing tool 1 of the present embodiment is provided with a reflecting portion 6 arranged outside the direction changing portion 3. The reflecting portion 6 includes a reflecting surface 6a facing the plurality of holes 4b provided in the discharge portion 4. As shown in FIG. 13, the reflecting portion 6 is provided at such a position that the distal end portion 32 of the insertion portion 31 of the endoscope 30 positioned by the positioning portion 5 is arranged between the reflecting surface 6a and the plurality of holes 4b. Note that the shape of the reflecting surface 6a is not limited to a concave shape as shown in FIG. 13 but may be a planar shape.

Some endoscopes 30 are in a form that the recess portion 33 provided on the distal end portion 32 penetrates the distal end portion 32 as shown in FIG. 13. In the case of performing reprocessing for the endoscope 30 in which the recess portion 33 provided on the distal end portion 32 is a through hole, using the endoscope reprocessing tool 1 of the present embodiment, fluid discharged from the plurality of holes 4b flows through the recess portion 33, abuts the reflecting surface 6a of the reflecting portion 6 and flows along an outer circumferential surface of the distal end portion 32 on an opposite side of the plurality of holes 4b.

According to the endoscope reprocessing tool 1 of the present embodiment, since it is possible to cause fluid that flows into the recess portion 33 after being discharged from the plurality of holes 4b to flow along the outer circumferential surface of the distal end portion 32 of the endoscope 30, it is also possible to focus on performing reprocessing on the outer circumferential surface of the distal end portion 32.

Figure 14:
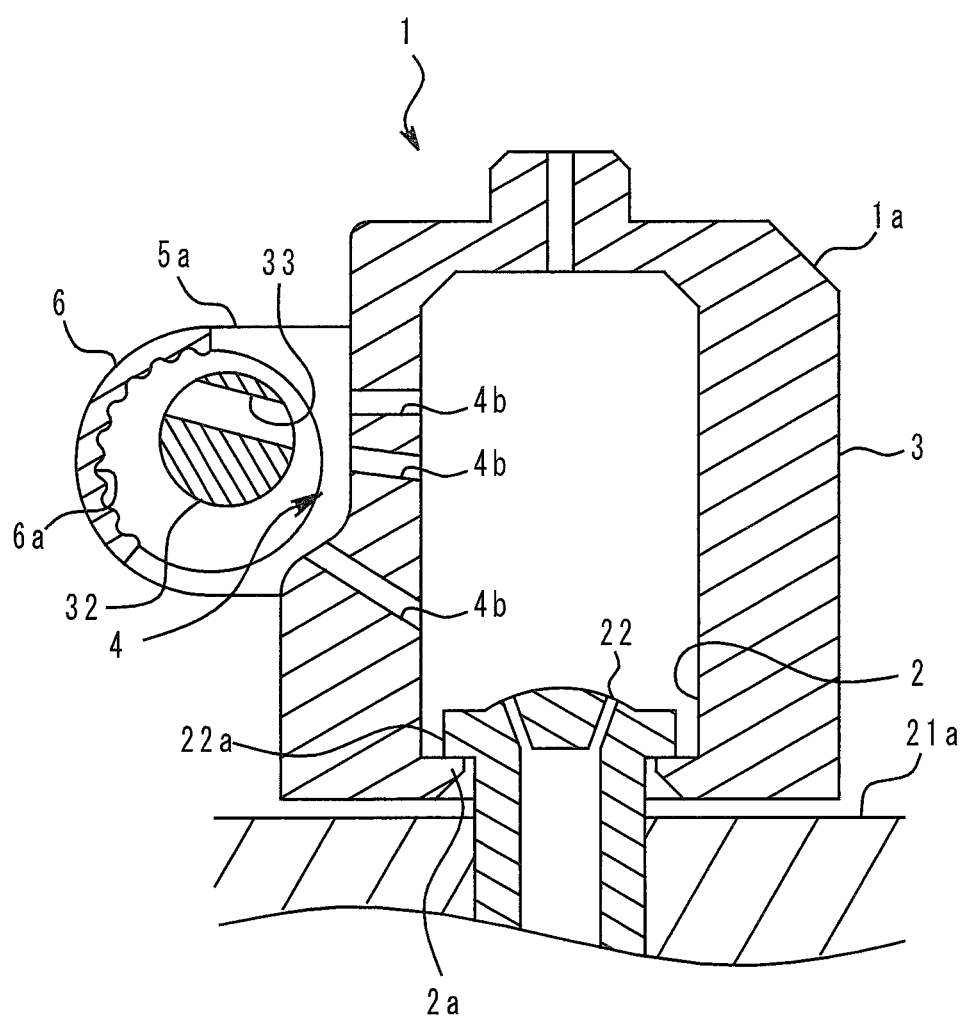
FIG. 14 is a diagram showing a modification of the endoscope reprocessing tool of the third embodiment.

Note that the reflecting surface 6a may be provided with fine irregularities as in a modification of the present embodiment shown in FIG. 14. By providing irregularities on the reflecting surface 6a as in the present modification, fluid discharged from the plurality of holes 4b flows spreading in various directions by abutting the reflecting surface 6a. Therefore, according to the endoscope reprocessing tool 1 of the present modification, it is possible to cause fluid that flows into the recess portion 33 after being discharged from the plurality of holes 4b to flow along the outer circumferential surface of the distal end portion 32 of the endoscope 30 evenly.

Note that the endoscope reprocessing tool 1 of the present embodiment may have the second detachable portion 2b attached to/detached from the connector 25 provided on the bottom face 21a of the reprocessing basin 21 as in the first modification of the first embodiment shown in FIG. 8. Further, the endoscope reprocessing tool 1 of the present embodiment may have the third detachable portion 2c or the fourth detachable portion 2d configured to generate urging force pressing the connection portion 2 to the bottom face 21a of the reprocessing basin 21 as in the second or third modification of the first embodiment shown in FIG. 9 or 10.

Further, the endoscope reprocessing tool 1 of the present embodiment may be in a form of being fitted to the nozzle 27 provided on the bottom face 21a of the reprocessing basin 21 of the endoscope reprocessor 20 and configured to discharge fluid in a direction crossing the gravity direction like the endoscope reprocessing tool 1 of the second embodiment shown in FIG. 11.

Fourth Embodiment

A fourth embodiment of the present invention will be described below. Only points different from the first embodiment will be described below. Components similar to those of the first embodiment will be given the same reference numerals, and description of the components will be appropriately omitted.

Figure 15:
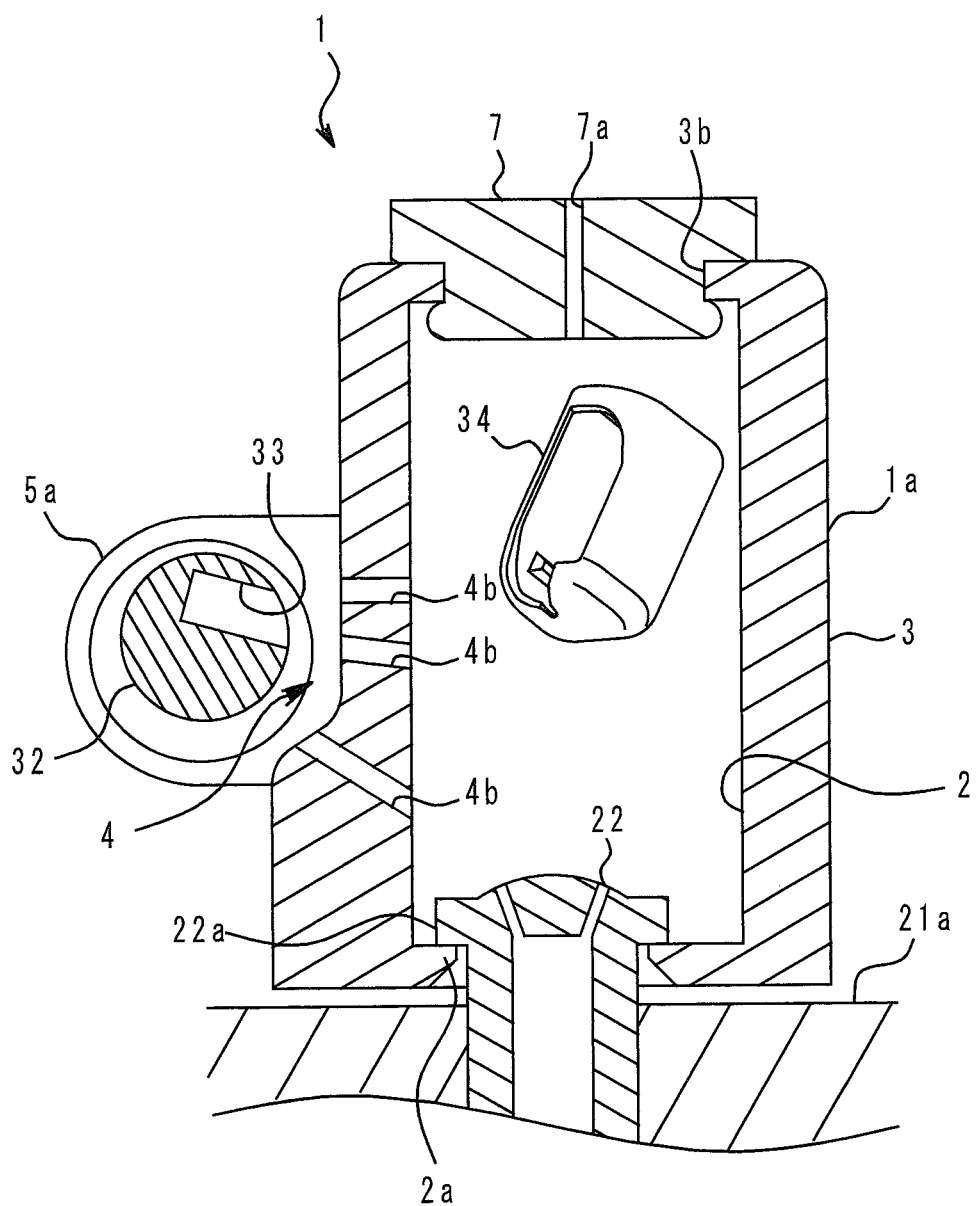
FIG. 15 is a cross-sectional view of an endoscope reprocessing tool of a fourth embodiment.

FIG. 15 shows an endoscope reprocessing tool 1 of the fourth embodiment. The endoscope reprocessing tool 1 of the fourth embodiment is provided with a gateway 3b that is a through hole penetrating the direction changing portion 3 from the outer surface to the internal space, and a cover 7 configured to open or close the gateway 3b. The cover 7 may be provided with a top surface cleaning hole 7a configured to discharge fluid toward the internal surface of the cover 23 arranged at the top of the reprocessing basin 21.

The internal space of the direction changing portion 3 of the present embodiment has a capacity capable of accommodating one or more accessories 34 of the endoscope 30, and the gateway 3b has a size capable of causing the accessories 34 to pass through. The kind and number of the accessories 34 are not especially limited. In the shown embodiment, the accessory 34 is a cap attachable to/detachable from the distal end portion 32 of the endoscope 30, which covers a part of the distal end portion 32 as an example. Note that, the accessory 34 may be a treatment instrument raising base removed from the distal end portion 32 of the endoscope 30 or may be a button removed from the endoscope 30.

In the case of performing reprocessing for the distal end portion 32 of the endoscope 30 using the endoscope reprocessing tool 1 of the present embodiment, it becomes possible to, if the one or more accessories 34 have been accommodated in the internal space of the direction changing portion 3, perform reprocessing for the accessories 34 also using fluid discharged from the fluid outlet 22.

Note that the endoscope reprocessing tool 1 of the present embodiment may have the second detachable portion 2b attached to/detached from the connector 25 provided on the bottom face 21a of the reprocessing basin 21 as in the first modification of the first embodiment shown in FIG. 8. Further, the endoscope reprocessing tool 1 of the present embodiment may have the third detachable portion 2c or the fourth detachable portion 2d configured to generate urging force pressing the connection portion 2 to the bottom face 21a of the reprocessing basin 21 as in the second or third modification of the first embodiment shown in FIG. 9 or 10.

Further, the endoscope reprocessing tool 1 of the present embodiment may be in a form of being fitted to the nozzle 27 provided on the bottom face 21a of the reprocessing basin 21 of the endoscope reprocessor 20 and configured to discharge fluid in a direction crossing the gravity direction like the endoscope reprocessing tool 1 of the second embodiment shown in FIG. 11.

Further, the endoscope reprocessing tool 1 of the present embodiment may be provided with the reflecting surface 6a facing the plurality of holes 4b provided in the discharge portion 4 like the endoscope reprocessing tool 1 of the third embodiment shown in FIG. 13.

Fifth Embodiment

A fifth embodiment of the present invention will be described below. Only points different from the first embodiment will be described below. Components similar to those of the first embodiment will be given the same reference numerals, and description of the components will be appropriately omitted.

Figure 16:
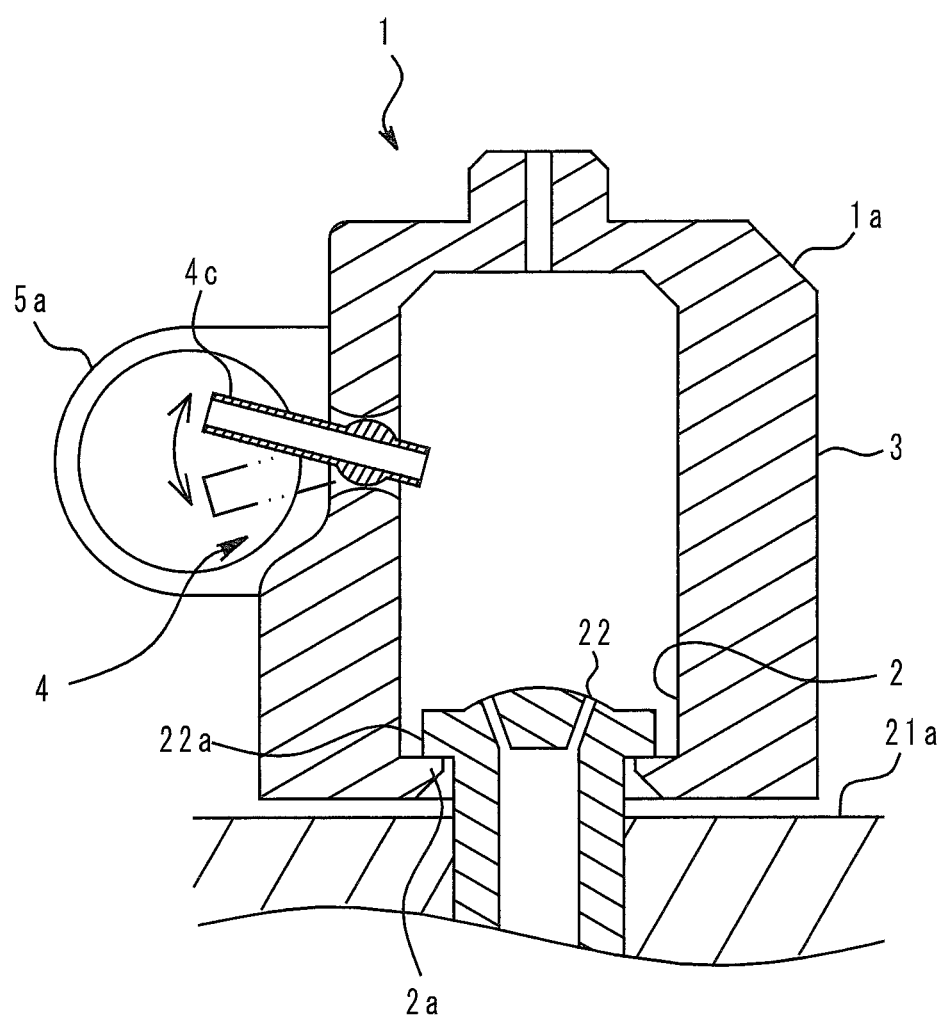
FIG. 16 is a cross-sectional view of an endoscope reprocessing tool of a fifth embodiment.

FIG. 16 shows an endoscope reprocessing tool 1 of the fifth embodiment. The discharge portion 4 of the endoscope reprocessing tool 1 of the fifth embodiment is provided with a nozzle 4c capable of changing a fluid discharge direction to the gravity direction. The nozzle 4c communicates with the internal space of the direction changing portion 3 and is attached to the direction changing portion 3 so as to rotate around a horizontal axis.

Figure 17:
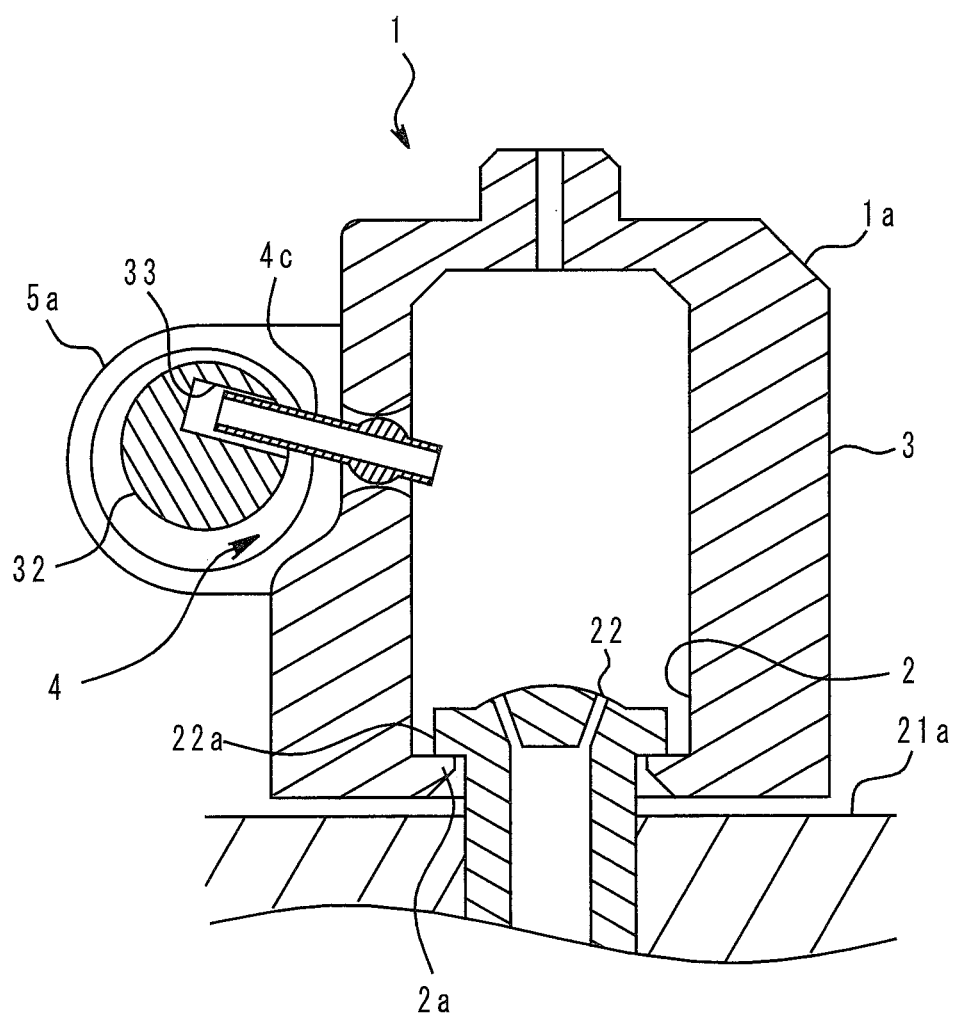
FIG. 17 is a cross-sectional view showing a case of performing reprocessing for a distal end portion of an endoscope using the endoscope reprocessing tool of the fifth embodiment.

The nozzle 4c projects from the outer surface of the direction changing portion 3. A distal end portion of the nozzle 4c projecting from the outer surface of the direction changing portion 3 can be inserted into the recess portion 33 provided on the distal end portion 32 of the endoscope 30 positioned by the positioning portion 5 as shown in FIG. 17.

Therefore, in the case of performing reprocessing for the distal end portion 32 of the endoscope 30 using the endoscope reprocessing tool 1 of the present embodiment, it is possible to certainly cause fluid used for reprocessing to flow into the depth of the recess portion 33.

Further, since the nozzle 4c of the present embodiment can change a fluid discharge direction to the gravity direction by rotating, it is possible to, even if the opening direction of the recess portion 33 of the distal end portion 32 positioned by the positioning portion 5 changes to the rotation direction around the longitudinal direction of the distal end portion 32, insert the distal end portion of the nozzle 4c into the recess portion 33 by changing the direction of the nozzle 4c.

Note that the endoscope reprocessing tool 1 of the present embodiment may have the second detachable portion 2b attached to/detached from the connector 25 provided on the bottom face 21a of the reprocessing basin 21 as in the first modification of the first embodiment shown in FIG. 8. Further, the endoscope reprocessing tool 1 of the present embodiment may have the third detachable portion 2c or the fourth detachable portion 2d configured to generate urging force pressing the connection portion 2 to the bottom face 21a of the reprocessing basin 21 as in the second or third modification of the first embodiment shown in FIG. 9 or 10.

Further, the endoscope reprocessing tool 1 of the present embodiment may be in a form of being fitted to the nozzle 27 provided on the bottom face 21a of the reprocessing basin 21 of the endoscope reprocessor 20 and configured to discharge fluid in a direction crossing the gravity direction like the endoscope reprocessing tool 1 of the second embodiment shown in FIG. 11.

Further, the endoscope reprocessing tool 1 of the present embodiment may be provided with the reflecting surface 6a facing the plurality of holes 4b provided in the discharge portion 4 like the endoscope reprocessing tool 1 of the third embodiment shown in FIG. 13.

Further, the endoscope reprocessing tool 1 of the present embodiment may be such that the accessories 34 of the endoscope 30 can be accommodated in the internal space of the direction changing portion 3 as the endoscope reprocessing tool 1 of the fourth embodiment shown in FIG. 15.

The present invention is not limited to the embodiments stated before but can be appropriately changed within a range not departing from the spirit or idea of the invention read from CLAIMS and the whole specification. An endoscope reprocessing tool with such changes is also included in the technical scope of the present invention.

What is claimed is:

1. An endoscope reprocessing tool comprising:
    a connection portion configured to be connected with a fluid outlet provided on a bottom face of a reprocessing basin of an endoscope reprocessor;
    a direction changing portion configured to change a flow direction of fluid discharged from the fluid outlet from a direction against a gravity direction to a direction crossing the gravity direction;
    a discharge portion configured to discharge the fluid direction-changed by the direction changing portion in the direction crossing the gravity direction; and
    a positioning portion configured to position a distal end portion of an endoscope so that the discharge portion and a recess portion provided on the distal end portion of the endoscope face each other.

2. The endoscope reprocessing tool according to claim 1, wherein the discharge portion includes a plurality of holes arrayed along an insertion direction of the distal end portion arranged so that the recess portion faces the discharge portion.

3. The endoscope reprocessing tool according to claim 2, wherein
    the discharge portion is configured having rows of the plurality of holes arrayed along the insertion direction; and
    a number of the rows is at least one.

4. The endoscope reprocessing tool according to claim 3, wherein
    the discharge portion has the rows in plurality in the gravity direction; and
    the plurality of rows include the plurality of holes arranged so that a crossing angle between a discharge direction and the gravity direction is smaller for a row farther from a gravity source.

5. The endoscope reprocessing tool according to claim 1, wherein the connection portion comprises a first detachable portion configured to be attached to/detached from a cleaning case attaching port for attaching/detaching a cleaning case.

6. The endoscope reprocessing tool according to claim 1, wherein the connection portion comprises a first detachable portion configured to be attached to/detached from an accessory cleaning nozzle attaching port for attaching/detaching an accessory cleaning nozzle.

7. The endoscope reprocessing tool according to claim 1, wherein the connection portion comprises a first detachable portion configured to be attached to/detached from a top surface cleaning nozzle attaching port for attaching/detaching a top surface cleaning nozzle, or attached to/detached from the top surface cleaning nozzle.

8. The endoscope reprocessing tool according to claim 1, wherein the connection portion comprises a second detachable portion configured to be attached to/detached from a self-disinfecting connector attaching port for attaching/detaching a self-disinfecting connector, or attached to/detached from the self-disinfecting connector.

9. An endoscope reprocessing tool comprising:
    a connection portion configured to be connected with a nozzle provided on a bottom face of a reprocessing basin of an endoscope reprocessor and configured to discharge fluid in a direction crossing a gravity direction; and
    a positioning portion configured to position a distal end portion of an endoscope so that the nozzle and a recess portion provided on the distal end portion of the endoscope face each other.

10. The endoscope reprocessing tool according to claim 9, comprising a discharge portion having a plurality of holes communicating with the nozzle and arrayed along an insertion direction of the distal end portion arranged so that the recess portion faces the nozzle.

11. The endoscope reprocessing tool according to claim 10, wherein the discharge portion is configured having rows of the plurality of holes arrayed along the insertion direction; and a number of the rows is at least one.

12. The endoscope reprocessing tool according to claim 11, wherein the discharge portion has the rows in plurality in the gravity direction; and the plurality of rows include the plurality of holes arranged so that a crossing angle between a discharge direction and the gravity direction is smaller for a row farther from a gravity source.

13. The endoscope reprocessing tool according to claim 1 comprising a reflecting portion comprising a reflecting surface facing the discharge portion and arranged so that the distal end portion positioned by the positioning portion is located between the discharge portion and the reflecting surface.

14. The endoscope reprocessing tool according to claim 1, wherein the direction changing portion has internal space capable of accommodating one or more accessories of the endoscope.

15. The endoscope reprocessing tool according to claim 1, wherein the discharge portion comprises a nozzle configured to be inserted into the recess portion, the nozzle being capable of changing an angle of a direction of discharging the fluid relative to the gravity direction.

* * * * *